United States Patent
Kravik et al.

(10) Patent No.: US 9,668,741 B2
(45) Date of Patent: Jun. 6, 2017

(54) AORTIC OCCLUDER WITH TENSIONED BALLOONS

(71) Applicant: Zoll Circulation, Inc., San Jose, CA (US)

(72) Inventors: Richard C. Kravik, Champlin, MN (US); James Greenberg, Zimmerman, MN (US); Crystal Xiong, Brooklyn Park, MN (US); Nao Lee, Brooklyn Park, MN (US)

(73) Assignee: Zoll Circulation, Inc., San Jose, CA (US)

( * ) Notice: Subject to any disclaimer, the term of this patent is extended or adjusted under 35 U.S.C. 154(b) by 204 days.

(21) Appl. No.: 14/460,124

(22) Filed: Aug. 14, 2014

(65) Prior Publication Data

US 2015/0051634 A1 Feb. 19, 2015

Related U.S. Application Data

(60) Provisional application No. 61/865,768, filed on Aug. 14, 2013.

(51) Int. Cl.
*A61B 17/12* (2006.01)
*A61B 5/0215* (2006.01)
*A61B 17/22* (2006.01)
*A61B 17/00* (2006.01)
*A61M 25/01* (2006.01)
*A61M 25/10* (2013.01)

(52) U.S. Cl.
CPC ...... *A61B 17/12109* (2013.01); *A61B 5/0215* (2013.01); *A61B 17/12036* (2013.01); *A61B 17/12045* (2013.01); *A61B 17/12136* (2013.01); *A61M 25/1034* (2013.01); *A61B 2017/00526* (2013.01); *A61B 2017/22054* (2013.01); *A61M 25/0102* (2013.01); *A61M 25/1011* (2013.01); *A61M 2025/1052* (2013.01); *A61M 2025/1095* (2013.01)

(58) Field of Classification Search
CPC ........ A61B 17/12022; A61B 17/12036; A61B 17/1204; A61B 17/12045; A61B 17/12109; A61B 17/12136; A61B 2017/22054; A61B 2017/22055; A61M 25/1027; A61M 25/1029; A61M 25/1034; A61M 2025/1013; A61M 2025/1052; A61M 2025/1059

See application file for complete search history.

(56) References Cited

U.S. PATENT DOCUMENTS

| | | | | |
|---|---|---|---|---|
| 5,868,776 A | * | 2/1999 | Wright | A61F 2/958 604/101.02 |
| 6,033,379 A | * | 3/2000 | Barra | A61M 25/10 604/103.11 |
| 6,146,370 A | | 11/2000 | Barbut | |
| 6,161,547 A | | 12/2000 | Barbut | |
| 6,165,199 A | | 12/2000 | Barbut | |
| 6,217,552 B1 | | 4/2001 | Barbut et al. | |

(Continued)

*Primary Examiner* — Ryan J Severson
*Assistant Examiner* — Christian Knauss
(74) *Attorney, Agent, or Firm* — John L. Rogitz (57) ABSTRACT

An aortic occluder catheter with expandable balloons for increasing cerebral blood blow has one or more balloons on a catheter shaft. To assist the balloon in bearing up against arterial blood flow while positioned retrograde in the aorta, the balloon is bonded to the catheter shaft in tension.

19 Claims, 9 Drawing Sheets

(56) References Cited

U.S. PATENT DOCUMENTS

| | | |
|---|---|---|
| 6,231,551 B1 | 5/2001 | Barbut |
| 6,355,010 B1 | 3/2002 | Barbut |
| 6,383,172 B1 | 5/2002 | Barbut |
| 6,530,894 B1 | 3/2003 | Barbut |
| 6,533,800 B1 | 3/2003 | Barbut |
| 6,555,057 B1 | 4/2003 | Barbut et al. |
| 6,565,552 B1 | 5/2003 | Barbut |
| 6,595,963 B1 | 7/2003 | Barbut |
| 6,595,980 B1 | 7/2003 | Barbut |
| 6,643,415 B1 | 11/2003 | Fukai et al. |
| 6,743,196 B2 | 6/2004 | Barbut et al. |
| 6,830,579 B2 | 12/2004 | Barbut |
| 6,848,448 B1 | 2/2005 | St. Germain et al. |
| 6,887,227 B1 | 5/2005 | Barbut |
| 6,942,686 B1 | 9/2005 | Barbut et al. |
| 7,340,298 B1 | 3/2008 | Barbut |
| 7,452,352 B2 | 11/2008 | Barbut |
| 7,635,376 B2 | 12/2009 | Barbut |
| 7,867,195 B2 | 1/2011 | Barbut et al. |
| 7,927,268 B1 | 4/2011 | St. Germain et al. |
| 7,993,324 B2 | 8/2011 | Barbut |
| 8,075,584 B2 | 12/2011 | Barbut |
| 8,137,374 B2 | 3/2012 | Barbut |
| 8,221,383 B2 | 7/2012 | Barbut |
| 2002/0115982 A1* | 8/2002 | Barbut ............ A61B 5/0215 604/509 |
| 2007/0135793 A1 | 6/2007 | Barbut et al. |
| 2007/0239135 A9 | 10/2007 | Barbut |
| 2010/0094330 A1 | 4/2010 | Barbut |
| 2011/0106132 A1 | 5/2011 | Barbut et al. |
| 2012/0089167 A1 | 4/2012 | Barbut |

\* cited by examiner

AORTIC OCCLUDER WITH TENSIONED BALLOONS

FIELD OF THE INVENTION

The present application relates generally to aortic occluders with pre-tensioned balloons.

BACKGROUND OF THE INVENTION

In the present assignee's U.S. Pat. No. 6,743,196, incorporated herein by reference, devices and methods are disclosed for partially or completely occluding the aorta temporarily to augment cerebral perfusion. As understood herein, a device that is positioned retrograde to blood flow in the aorta faces high fluid pressure against one or more of its operative components, presenting challenges that otherwise would not be presented were the device to be located in a vessel of less harsh fluid flow dynamics.

SUMMARY OF THE INVENTION

Accordingly, a catheter includes an elongate member having proximal and distal ends and proximal and distal regions. A first expandable member is mounted on the distal region of the elongate member. The first expandable member is inflatable with fluid through at least one lumen in the elongate member to cause the expandable member to expand from an empty configuration to an expanded configuration. As disclosed in greater detail below, the first expandable member is disposed on the elongate member in tension such that the first expandable member is pre-loaded with tensile stress in the empty configuration. This enables the expandable member to better bear up against arterial blood flow when the expandable member is positioned retrograde in the aorta. During use, the flexible distal region allows the elongate member to conform to a portion of the aorta such as the descending aorta while the first expandable member is positioned in the portion of the aorta and is at least partially expanded to increase cerebral perfusion.

A second expandable member can also be mounted on the elongate member proximal the first expandable member and may be pre-loaded onto the elongate member with tensile stress. The expandable members can be cylindrical expandable balloons each having an outer surface and an enclosed chamber.

A port can be formed in the elongate member and can communicate with a pressure monitoring lumen in the elongate member for establishing fluid communication between the port and a pressure monitoring device that is engageable with the pressure monitoring lumen. In some embodiment a stiffening element is inserted into a lumen of the elongate member. The proximal region of the elongate member provides stability to prevent migration during use.

In another aspect, a medical device for partial aortic occlusion for cerebral perfusion augmentation includes a catheter body and a first expandable balloon disposed on the catheter body and pre-loaded with tensile stress prior to expansion of the balloon under the influence of an inflation fluid.

In another aspect, a method for making an aortic occlusion device includes disposing an expandable member on a catheter shaft formed with a lumen through which fluid can be provided to an interior of the expandable member. The method also includes holding the expandable member on the catheter shaft with tensile stress on the expandable member such that the expandable member is always in tension.

The details of the present application, both as to its structure and operation, can best be understood in reference to the accompanying drawings, in which like reference numerals refer to like parts, and in which:

DETAILED DESCRIPTION OF THE PREFERRED EMBODIMENT

For convenience, portions of the above-incorporated patent are first discussed.

Figure 1:
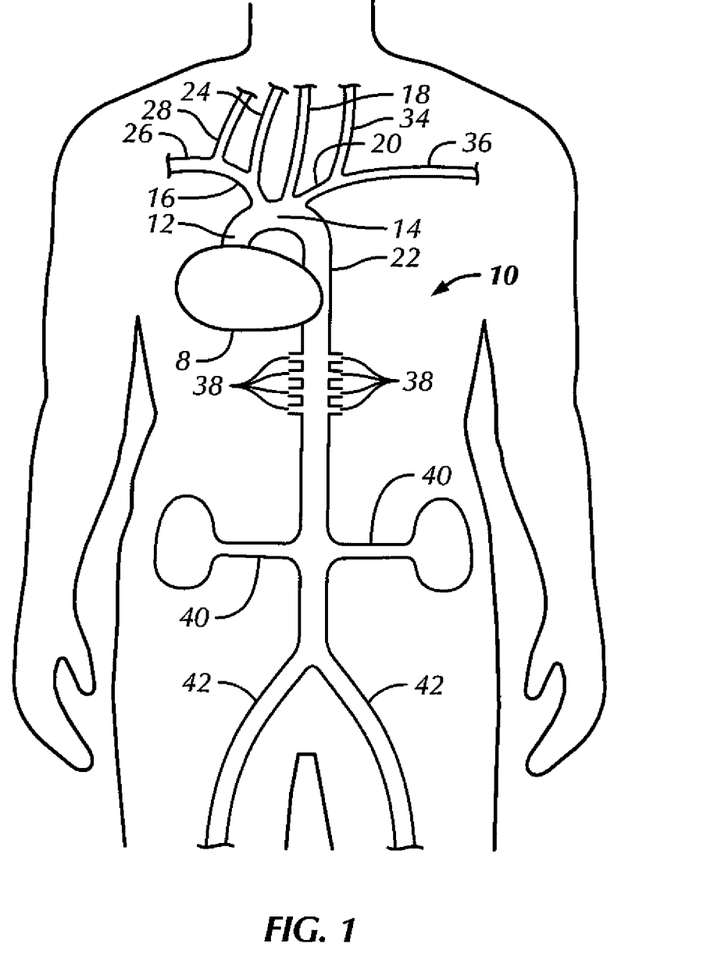
FIG. 1 illustrates a patient's systemic arterial circulation.

Referring initially to FIG. 1, during systole, oxygenated blood leaving a patient's heart 8 enters the aorta 10, which includes the ascending aorta 12, aortic arch 14, and descending aorta 22. The aortic arch gives rise to the brachiocephalic trunk 16, left common carotid artery 18, and left subclavian artery 20. The brachiocephalic trunk branches into the right common carotid artery 24 and right subclavian artery 26. The right and left subclavian arteries, respectively, give rise to the right vertebral artery 28 and left vertebral artery 34. The descending aorta gives rise to a multitude of arteries, including lumbar (i.e., spinal) arteries 38, which perfuse the spinal cord, renal arteries 40, which perfuse the kidneys, and femoral arteries 42, which perfuse the lower extremities.

Figure 2A:
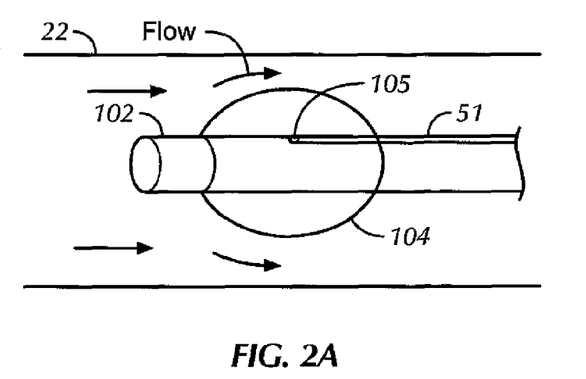
FIG. 2A illustrates an embodiment of devices for providing partial occlusion of a vessel.

In one embodiment as shown in FIG. 2A, an aortic occluder or obstruction device includes an elongate catheter 102 having a proximal end and a distal end, shown here positioned within descending aorta 22 retrograde to blood flow indicated by arrows "flow". That is, the distal end of the catheter 102 faces against arterial blood flow. The distal end has expandable member 104, e.g., a balloon. The balloon 104 communicates with an inflation lumen 51 through a port 105.

Figure 2B:
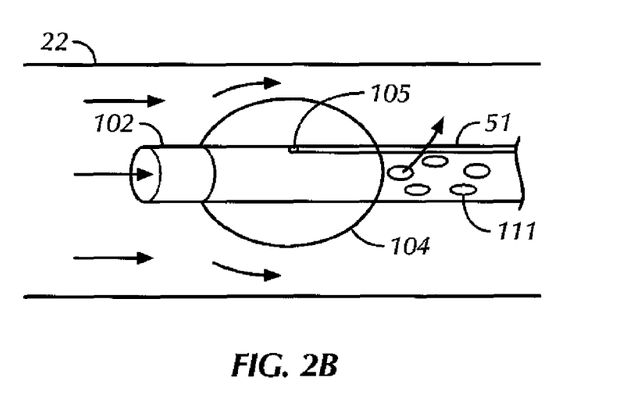
FIG. 2B illustrates another embodiment of the devices for providing partial occlusion of a vessel.

In another embodiment, depicted in FIG. 2B, plural ports 111 are included in the surface of a catheter 102 to allow blood flow through the distal end of the catheter 102 to pass through a catheter downstream constrictor 104.

Figure 3:
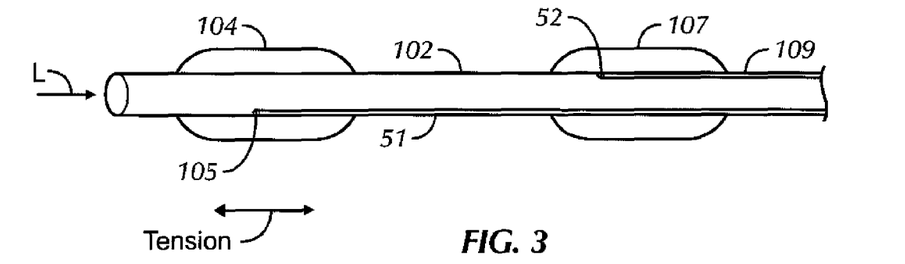
FIG. 3 illustrates another embodiment of a device with two expandable members for providing partial occlusion of a vessel.

In yet another embodiment as shown in FIG. 3, the catheter 102 has a proximal end, a distal end, a first expandable member 104 and second expandable member 107, e.g., balloons, and in certain embodiments elongate balloons, mounted and spaced from each other. The balloon 104 communicates with the inflation lumen 51 through a first port 105. On the other hand, the balloon 107 communicates with its inflation lumen 109 through a second port 52. The balloons 104, 107 are thus able to be inflated independent of each other, or, in other embodiments, are inflated from a common inflation lumen.

It will be understood that the constrictor, when implemented as a balloon, can be of any shape that is suitable for use in the aorta. An elongate balloon (e.g., balloons 104 and 107 in FIG. 3), elliptical or sausage-shape, may be used because this shape is more stable within rapidly flowing blood, although a spherical balloon may also be used.

In certain embodiments, the catheter can be equipped with blood pressure measuring capabilities proximal and/or distal to one or each expandable member. In example embodiments the blood pressure measuring devices may include a manometer mounted on the catheter or a channel communicating with a transducer at the proximal end and a port at the distal end of the catheter. Blood pressure measuring may also be accomplished by use of a fiber optic in vivo pressure transducer, or a Radi pressure wire.

Figure 4:
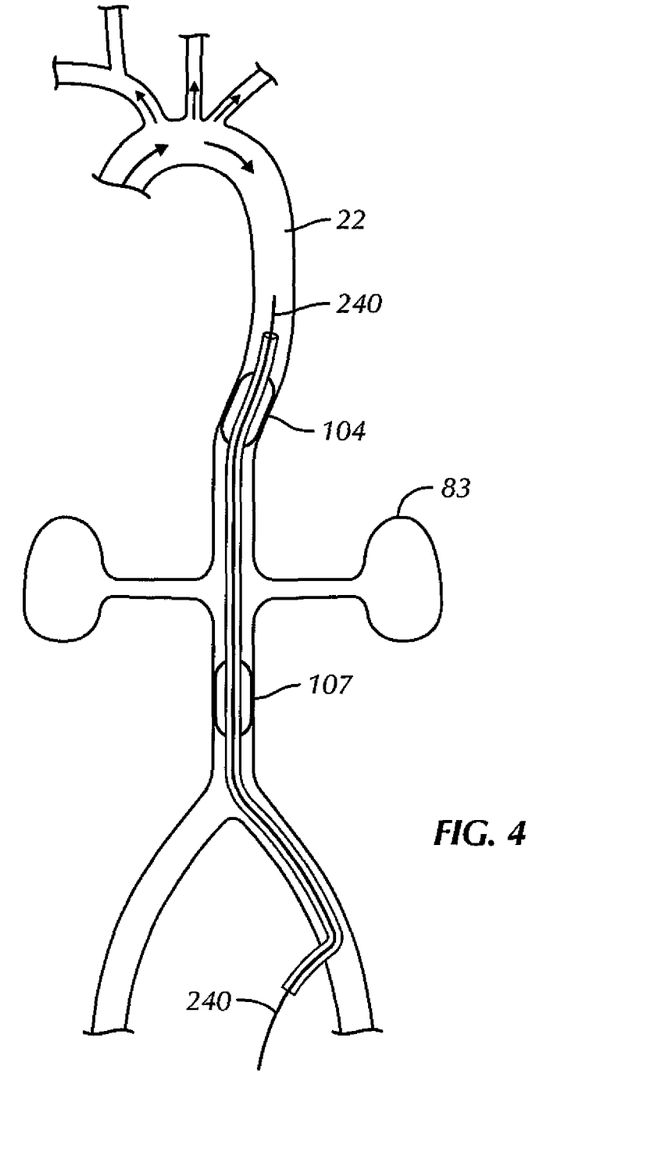
FIG. 4 illustrates deployment of the device shown in FIG. 3 in the aorta.

In an example use, the catheter is inserted into the descending aorta 22, and advanced to a position such that the first constricting balloon 104 is upstream of the renal arteries, celiac, and superior mesenteric artery, and the second constricting balloon 107 is downstream of these arteries as shown in FIG. 4. A two-balloon device permits independent regulation and adjustment of cerebral blood flow and renal blood flow. The downstream balloon 107 can be first expanded while measuring cerebral blood flow until the desired increase over baseline is obtained, e.g., 25-50% increase. This step will also result in increased blood flow to the renal and superior mesenteric arteries. If this step results in inadequate cerebral blood flow increase, then upstream balloon 104 can then be expanded to constrict upstream the renal and superior mesenteric arteries until the desired cerebral blood flow increase is obtained. Deployment of the upstream constrictor reduces blood flow to the renal and superior mesenteric arteries as compared with blood flow before deployment of the upstream constrictor.

If the deployment of the downstream balloon 107 produces the desired increase in cerebral blood flow, then the upstream balloon 104 need not be deployed in certain procedures. In other procedures, the upstream balloon 104 is deployed so that constriction in the downstream balloon 107 can be reduced, thereby partially relieving the renal and superior mesenteric arteries of increased flow. It will be understood that inclusion of a balloon downstream is desirable in some cases because it allows the surgeon to maintain renal blood flow at or above baseline while increasing blood flow to the brain. It may also be desirable to achieve constriction predominantly downstream of the renal arteries that supply blood to the kidneys 83 to avoid obstructing the spinal arteries that lie upstream the renal arteries. It may also be desirable to have both balloons 107 and 104 partially inflated, rather than either balloon fully inflated, to avoid blocking arteries that branch from the aorta.

Alternatively, both balloons may be inflated simultaneously until a desired increase in cerebral flow is achieved. In this manner, flow to the renal arteries will be maintained at substantially the initial baseline flow. If it is desired to further adjust renal blood flow while maintaining the cerebral blood flow and/or increase in proximal aortic pressure, the two balloons can be simultaneously adjusted, e.g., one increased and one decreased, until the desired renal blood flow is achieved.

It is to be understood that one objective for the devices and methods described herein is to increase cerebral blood flow following a stroke. Expansion of a constrictor in the descending aorta produces increased blood pressure upstream of the constrictor, which leads to increased cerebral blood flow. A small change in upstream blood pressure, however, can produce a very large change in cerebral blood flow. Cerebral blood flow can be measured by transcranial Doppler, functional MRI, CT scan, PET scan, SPECT scan, or any other suitable technique known in the art. In certain procedures therefore, it may be desirable to adjust expansion of the constrictors 107 and/or 104 in response to measured cerebral blood flow increase instead of, or in addition to, measured blood pressure increase upstream the constrictor and/or measured blood pressure decrease downstream the constrictor. If cerebral blood flow is to be used as a measure, then a baseline blood flow is measured before expansion of the constrictor. The constrictor is then expanded while measuring blood flow until a desired increase in flow is achieved. Typically, the desired increase will be 50 percent or greater, 60 percent or greater, 70 percent or greater, 80 percent or greater, 90 percent or greater, or 100 percent or greater of baseline blood flow, or more than 100 percent. The amount of increased cerebral blood flow will depend on a variety of factors including the patient's baseline blood pressure. If the blood pressure is excessively high, it may be desirable to achieve a smaller increase in cerebral blood flow, so as not to increase the proximal aortic pressure to an excessive value. In addition, the increase in the amount of pressure or flow achievable will also depend on baseline conditions. For example, the lower the baseline aortic pressure, the larger the pressure increase achievable.

The aorta is a curved vessel that bends as it progresses from the aortic arch to the branch at the femoral arteries, as shown in FIG. 4. When one or both of the occlusion balloons are inflated, the blood pressure in the aorta upstream of the occluder(s) is caused to increase, while the pressure below the occluder(s) is decreased from baseline. With significant obstruction, e.g., 85-95 percent diameter obstruction, this pressure drop along the length of the occlusion balloon(s) can be significant, on the order of 20-150 mmHg. This pressure drop, by acting on the cross-sectional area of the occlusion balloon(s) creates a substantial longitudinally directed compressive force on the shaft of the catheter. The pressure drop and force are pulsatile in nature (due to systole and diastole) and tend to push the occlusion device down and back up.

To minimize this motion it is desirable to reinforce the catheter shaft. One way to reinforce the shaft is to incorporate stiffening mandrel or stylet 240. This may be incorporated within the shaft at the point of manufacture or it may be introduced within the shaft once the occlusion device is positioned in the aorta. Furthermore, the mandrel or stylet 240 may be a solid wire, or may be a hollow tube, such as a hypotube.

In use, a guidewire is advanced into the aorta. The catheter 102 is advanced over the guidewire. Once the catheter is in place, the guidewire is removed and a mandrel 240 can be advanced into a lumen of the catheter until it reaches the proper position. In certain procedures, the mandrel has a curvature at the end to forcibly deflect the occlusion balloon(s) to the wall of the aorta. The mandrel is then periodically rotated to reposition the constrictors 104 and 107 at a new location along the lumenal wall of the aorta 22. This periodic movement ensures that branching vessels are not deprived of blood for too long.

The distal balloon 104 and proximal balloon 107 may both be fabricated of an elastomeric material such as blow molded polyurethane. Both can be molded to have an initial inflated diameter of about 10 mm, with a capability of being inflated to 25 mm with increasing pressure. It is anticipated that other sizes could be utilized. For example, the distal balloon could be larger than the proximal balloon, with an initial diameter of 15 mm, and a capability of being inflated to 35 mm with increasing pressure.

Each balloon may have two cylindrical waists which are used in the securing of the balloons to the catheter shaft 102. The balloons may be adhesively bonded to the catheter shaft, or may be thermally or laser bonded. Other suitable means of joining the balloons are also contemplated.

Figure 5A:
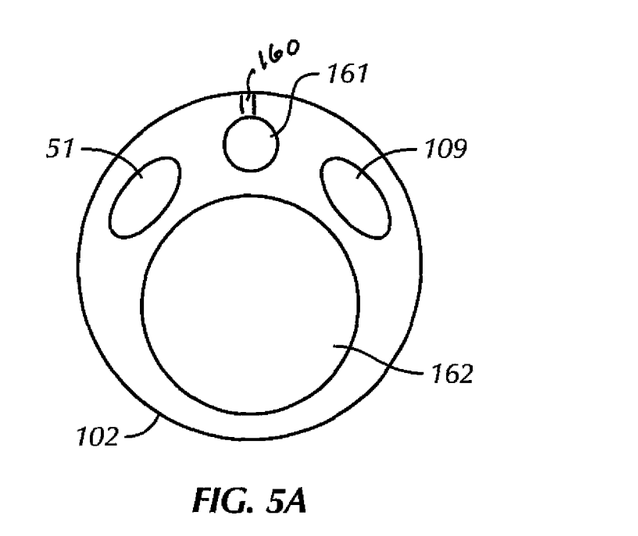
FIG. 5A illustrates a side view of another embodiment of a device for providing partial occlusion of a vessel with portions cut away to reveal interior structure
Figure 5B:
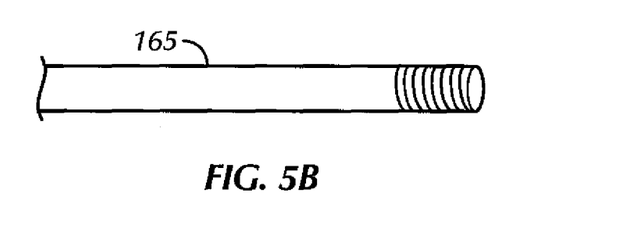
FIG. 5B illustrates a hypotube with an atraumatic tip.
Figure 5C:
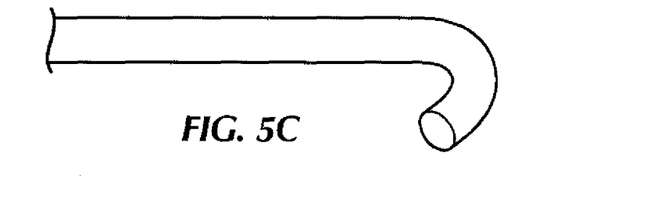
FIG. 5C illustrates a pig-tailed atraumatic tip for a catheter.
Figure 5D:
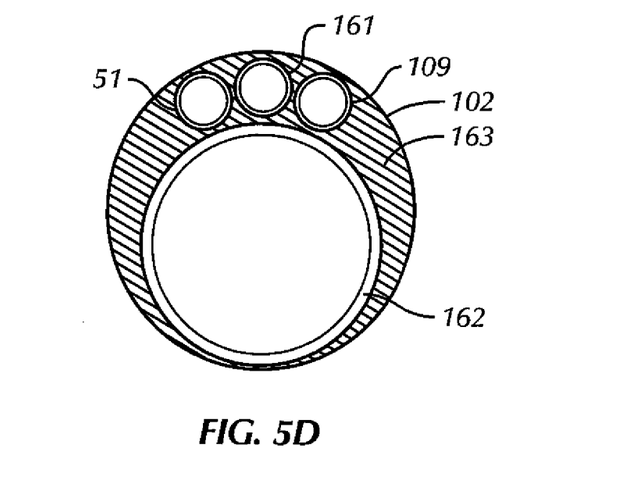
FIG. 5D is a cross-sectional view of an alternative design of a catheter.

As shown, the balloons 104 and 107 are mounted on the distal region of the catheter shaft 102. In this embodiment, the catheter shaft structure can include a unitary extruded multi-lumen tube as shown in FIG. 5A, which extends for the full length of the device, with the exception of a soft tip attached at the distal end. The multi-lumen tube with, e.g., lumens 51, 161, 109, 162 is preferably formed of an extrudable polymer, such as Pebax, polyethylene, polyurethane, polypropylene, or nylon. Alternatively, the shaft structure could be fabricated as illustrated in FIG. 5D, in which individual thin walled tubes are used to define each lumen, and are preferably formed of a material suitable for very thin walls, such as polyimide or polyimide composite structures. As illustrated, the inter-balloon pressure monitoring lumen 161, and the inflation lumens 51 and 109 are defined by thin polyimide tubes, and the wire lumen can be defined by a thin walled composite tube of PTFE, braided metal, and polyimide. The four thin walled tubes 51, 109, 161, and 162 can then be encased within an extrusion or coating 163 of a polymeric material, such as Pebax, polyurethane, polyethylene, or other suitable polymer.

In the example shown, four lumens are within the catheter 102, namely, a wire lumen 162, an inter-balloon pressure monitoring lumen 161, and two inflation lumens 51 and 109, one each for delivery of inflation fluid to each balloon. Each balloon can be inflated via respective ports which allow fluid communication between the inflation lumen and the balloon interior. The portions of the inflation lumens which extend distally of their respective ports can be occluded by suitable means such as an adhesive plug.

The inter-balloon pressure monitoring lumen 161 can be in fluid communication with the surrounding blood via a port 160 in the tubing wall. When a suitable fluid such as saline resides in this lumen during use of the device, the blood pressure at the port is transmitted down the lumen to a pressure transducer. When the device is positioned as intended in some examples, with the two balloons spanning the renal arteries, the renal blood pressure can be monitored, providing input to influence the degree of balloon inflation of the two balloons.

The wire lumen 162 can be used during initial placement with a guide wire, which may be later removed, or may be left in place. The remaining space within the wire lumen may be used to monitor the blood pressure upstream from the distal balloon 104. This is another input which may be used to influence the degree of inflation of one or both balloons.

As mentioned, the shaft structure can also include a soft (atraumatic) tip. The tip can be attached to the distal end of the multi-lumen tube by suitable means such as a thermal or adhesive butt joint. The single lumen within the tip creates an extension of the wire lumen. The tip may be straight (FIG. 5B), and may further include a tapering dimension on the outer and inner diameters. The tip may also be fabricated in a "pigtail" shape as shown in FIG. 5C which straightens in the presence of a guide wire extending through the wire lumen, but returns to the curled shape upon removal of the guide wire. A pigtail shape reduces opportunities for trauma to the vessel.

The device as described provides the appropriate flexibility for smooth advancement over a guidewire, and may be introduced into the aorta without the need for fluoroscopic guidance. Radio-opaque markers can nonetheless be provided, in the instances where fluoroscopic guidance is utilized, or if a simple plate x-ray is used to assist in device positioning.

Figure 5E:
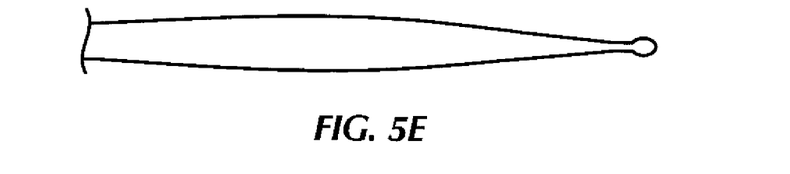
FIG. 5E illustrates a stylet for use in an occluder.

As mentioned previously, when one or both balloons of a dual balloon device are inflated, significant longitudinal compressive forces can be imposed on the catheter. To help stabilize the device, the shaft structure of this embodiment provides for subsequent introduction of a stiffening element, such as a wire stylet, or a hypotube. If a wire stylet is used, the initial delivery guidewire is removed, to make room for the stylet. The stylet as shown in FIG. 5E can be tapered and can have a bulbous tip, facilitating smooth introduction into the wire lumen. The stylet may be sufficiently large that it occupies most of the available lumen. However, it is preferable to still maintain a clearance between the stylet and the wall of the wire lumen, to maintain the ability to monitor blood pressure. Alternately, the stylet may incorporate a pressure transducer mounted near the tip, in which case, the wire lumen can be fully occupied by the stylet.

Figure 5F:
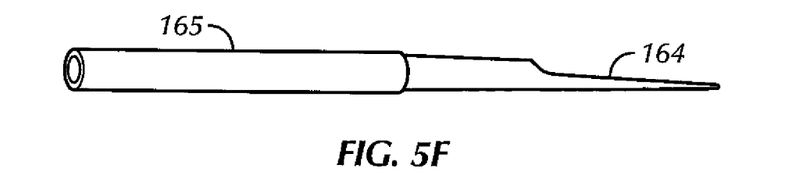
FIG. 5F illustrates a hypotube having a skive.

If a hypotube is used as the stiffening element, the initial guide wire need not be removed, as long as the inner diameter of the hypotube is large enough to accommodate the guide wire. The hypotube can have a diameter slightly less than the wire lumen diameter, and a tapering outer diameter toward the distal end, to facilitate smooth tracking in the wire lumen. A hypotube 165 as shown in FIG. 5F can further incorporate a "skive" 164 to gain further flexibility near the distal end to facilitate smooth tracking. Alternately, the distal portion of the hypotube can have a helical cut of progressively tighter pitch as shown in FIG. 5B or other patterns of removed material in the hypotube 165 to facilitate a gradually increasing flexibility. The inner lumen of the hypotube can be used as a pressure monitoring lumen for the upstream aortic pressure. The hypotube may be coated both on the internal surface by a lubricious and non-thrombogenic material, such as a hydrophilic coating, FIFE liner, or a paralene coating. With both the wire stylet and the hypotube stiffening elements, it is contemplated that they could be incorporated initially within the device, as opposed to introduced subsequent to positioning of the balloons. If the stiffening element is initially incorporated into the shaft structure, it is preferred to connect somewhere in the distal region of the stiffening element to the shaft tube, by suitable means such as an adhesive or thermal bonding.

Figure 6A:
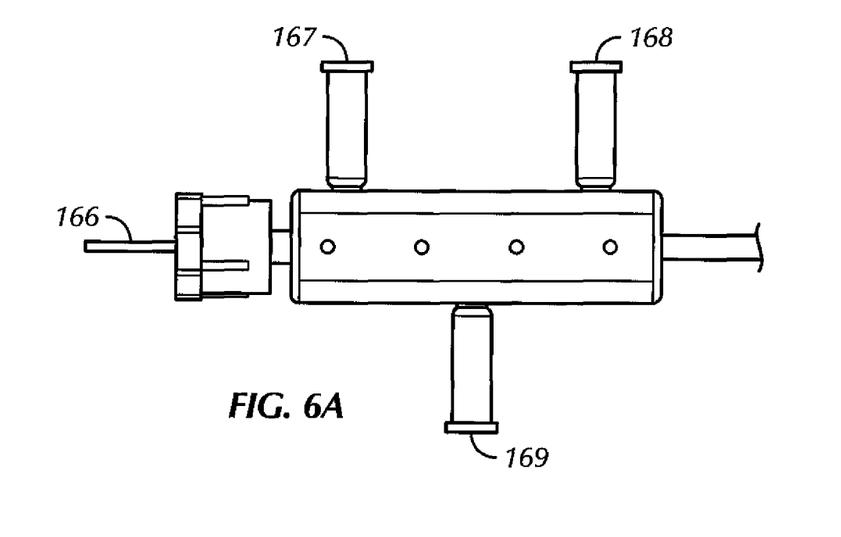
FIGS. 6A-6C show a manifold structure for engaging a proximal part of a catheter and further details of the catheter.

Referring to FIG. 6A, at the proximal end of the device, a manifold structure can be connected to the shaft structure. The manifold structure can include luer fittings that communicate with each of the lumens. For example, a pressure fitting 169 communicates with the pressure monitoring lumen 161, a first inflation fitting 167 communicates with the proximal balloon inflation lumen 109, and a second inflation fitting 168 communicates the with distal balloon inflation lumen 51. The entire shaft structure and balloons may be preferably coated with a lubricious and non-thrombogenic coating, such as a hydrophilic coating, and/or a heparin coating. Other anti-thrombogenic agents are also possible, such as phospholcholine.

Figure 6B:
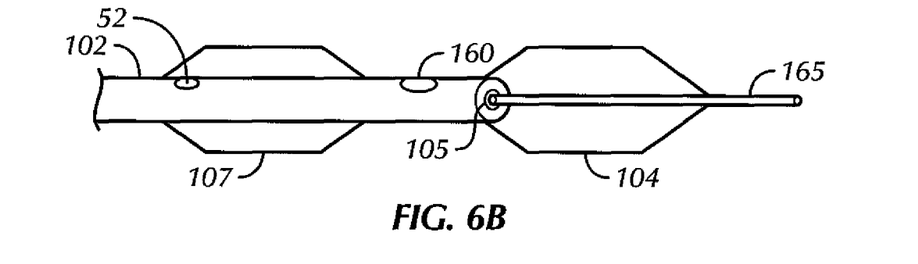
Figure 6C:
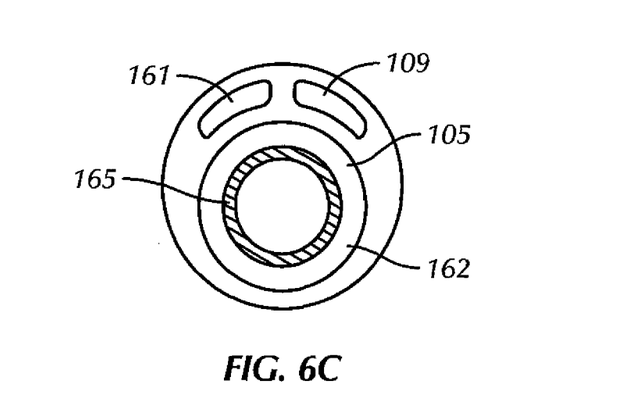

FIGS. 6B and 6C illustrate an additional embodiment for a dual balloon occlusion device, and uses an alternative shaft structure. The shaft structure can include two primary components, namely, a multi-lumen polymeric tube 102 and a hypotube 165. The hypotube in this embodiment is fabricated directly into the device. The multi-lumen tube can have three lumens as shown in FIG. 6B, and a main lumen 162 may be circular. The hypotube can reside within this lumen, and the remaining leftover annular space 105 may serve as the inflation lumen for the distal balloon. The proximal balloon inflation lumen can serve as the lumen for inflation of the proximal balloon, while the pressure monitoring lumen 161 may serve as the lumen used in connection with inter-balloon pressure monitoring.

In accordance with present principles, in addition to the stiffening techniques described above, to help the balloons 104, 107 of any of the above-disclosed embodiments bear up against the force of arterial blood flow when the catheter is positioned retrograde in the aorta, one or both of the balloon can be mounted to the catheter shaft in tension. For greater detail, refer back to FIG. 3.

As shown, at least the distal balloon, in one example, is disposed on the catheter shaft 102 in tension, and specifically with tensile stress having its principal direction vector "tension" substantially aligned the longitudinal axis "L" of the catheter. Thus, the pre-loading of tensile stress on the balloon is done prior to expanding the balloon with fluid and is done during manufacture such that the stress remains on the balloon. The proximal balloon may also be pre-loaded with tensile stress either of the same magnitude of the stress imposed on the distal balloon or a different, e.g., lesser, magnitude.

Pre-loading a balloon with tensile stress may be accomplished in one of several ways. In one example, the balloon is mechanically stretched in the longitudinal dimension and is held stretched during the bonding process. In this example, the proximal tube-like neck of the balloon is first bonded to the catheter shaft by disposing heat shrink tubing such as a Fluorinated Ethylene Propylene (FEP) sleeve around the proximal neck and then heating the proximal neck with catheter shaft inside it and heat shrink tubing surrounding it in a thermal bonding machine.

Then, a second piece of heat shrink tubing is disposed around the distal neck of the balloon and a lubricant or solvent such as Heptane applied between the distal balloon neck and catheter shaft. The balloon is then stretched using, e.g., pliers into a longitudinally tensioned configuration and while being held in the stretched position, the Heptane is dried using, e.g., an air gun. The distal portion of the balloon with heat shrink is then heated in the thermal bonding machine with the balloon held in the stretched configuration. Note that depending on how many balloons are used on the catheter and a particular balloon's relative position on the catheter, the above process can be reversed, i.e., the distal balloon neck is first bonded to the catheter and then the proximal neck is stretched away from the distal neck and bonded.

In another example the balloon is made of a material which shrinks when it is heated, and is initially bonded to the shaft in an ambient temperature lower than room temperature, such that when the catheter returns to room temperature, the balloon stretches as it heats up from the ambient temperature to which it was exposed during connection to the shaft. In another example the balloon is made of a material which shrinks when it is cooled, and is initially bonded to the shaft in an ambient temperature higher than room temperature, such that when the catheter returns to room temperature, the balloon stretches as it cools down from the ambient temperature to which it was exposed during connection to the shaft.

Figure 7:
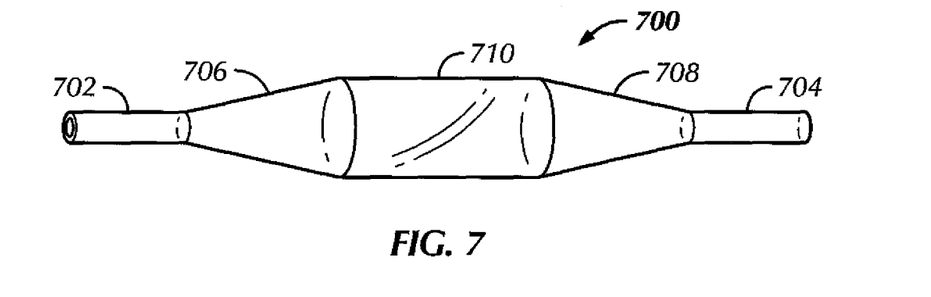
FIGS. 7-13 illustrate details of an example balloon bonding process.

FIGS. 7-13 illustrate above principles and additional details of an example balloon bonding process that can be used to manufacture a catheter according to the present principles. As shown in FIG. 7, a balloon 700 such as a seven French balloon is obtained. As shown, the balloon 700 has radially small proximal and distal necks 702, 704, each being integral with a respective proximal and distal conical segment 706, 708. In turn, the conical segments 706, 708 taper outwardly to join proximal and distal regions of a central radially enlarged portion 710.

Figure 8:
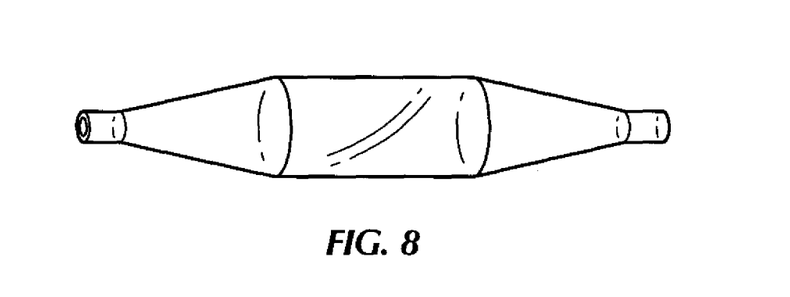

As shown in FIG. 8, the proximal and distal necks 702, 704 may first be trimmed in length using, e.g., a razor blade. In an example embodiment, the necks 702, 704 re trimmed to a length of between three and four millimeters. A catheter shaft 712 (FIG. 9) such as the one used for any of the catheters shown above is obtained and preferably wiped down using a lint free wipe. Appropriate settings are established for the thermal bonding machine, e.g., bonding temperature of 450 degrees Fahrenheit, bonding time sixteen seconds, bonding pressure equal to or greater than sixty pounds per square inch.

Figure 9:
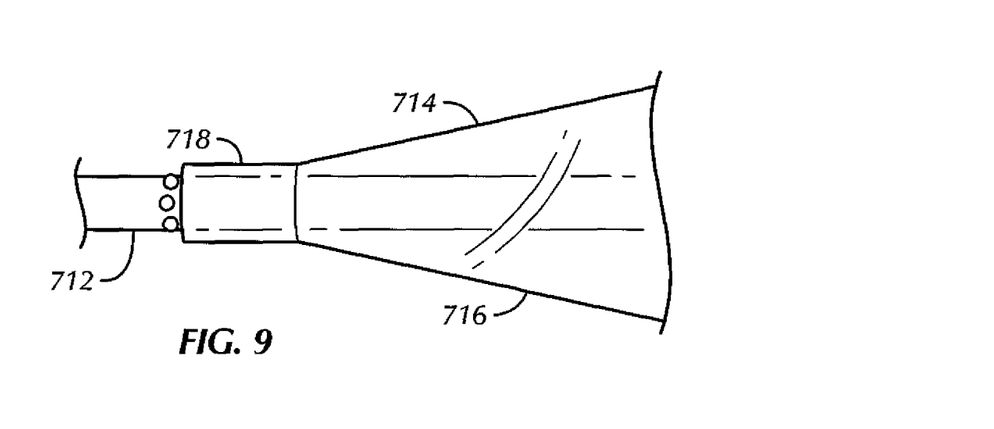
Figure 10:
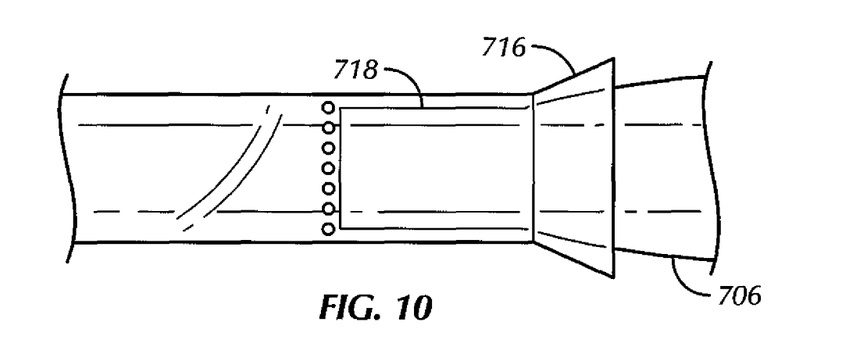

Next, as can be appreciated in reference to FIG. 9, a flaring tool can be used to flare an end of a heat shrink tubing 714 to establish a conical segment 716 that is flared outwardly as shown and that terminates in a tubular end segment 718. The balloon is slid down along the distal end of the catheter 712, in some cases while rotating the catheter 712 to facilitate sliding motion, and then the tubular end segment 718 of the heat shrink tubing 714 is slid over the proximal neck 702 of the balloon with the conical segment 716 of the heat shrink tubing 714 being located distal to the tubular end segment. Note that the proximal neck 702 and the rest of the balloon in FIG. 9 are between the heat shrink tubing 714 and the catheter 712 and thus are not visible in FIG. 9. However, FIG. 10 illustrates the proximal conical segment 706 of the balloon 700 being covered by the conical segment 716 of the heat shrink tubing 714 with the tubular end segment 718 of the heat shrink tubing 714 closely surrounding the proximal neck 702 of the balloon. The arrangement of FIG. 9 is established such that the conical segment 716 of the heat shrink tubing 714 covers the proximal conical segment 706 of the balloon, to protect the balloon during the bonding process.

The proximal end of the balloon, covered by the tubular end segment 718 of the heat shrink tubing 714, is placed into a groove of a clamp fixture associated with the thermal bonding machine and secured using a rubber clamp. The clamp fixture is engaged with the heating components of the bonding machine and the bonding machine activated according to the settings established above to bond the proximal end of the balloon to the catheter in part aided by the heat shrink tubing. After bonding, the catheter is removed from the bonding machine and allowed to cool.

Next, the distal neck 704 of the balloon is bonded to the catheter shaft as follows. A second piece of heat shrink tubing is flared as described above in the case of the first piece of heat shrink tubing 714 and then slid over the distal end of the catheter 712 with the flared end of the heat shrink tubing oriented toward the proximal end of the catheter 712. The balloon is pushed from its currently unbounded distal end toward the bonded proximal end, e.g., by hand, to decrease the length of the balloon, e.g., by one-half. A lubricant or solvent such as Heptane can then be applied to the distal balloon neck and catheter shaft, and then the balloon pulled back to its full and untensioned length.

Figure 11:
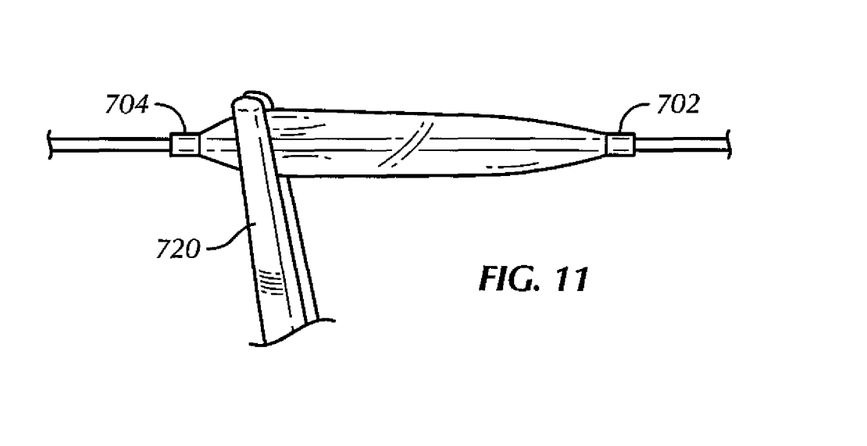
Figure 12:
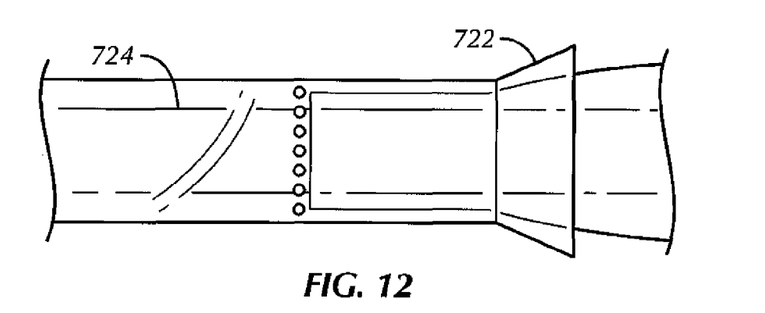
Figure 13:
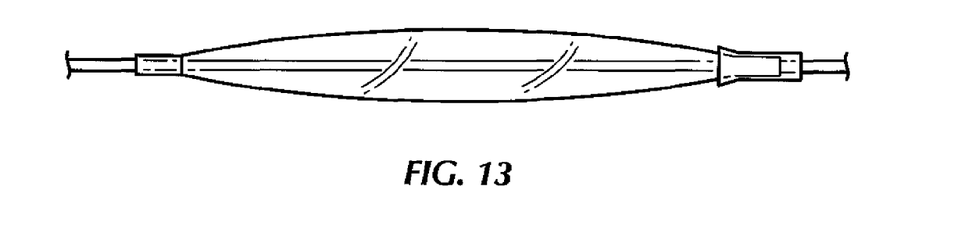

Next, as shown in FIG. 11, a tool 720 such as stretch pliers can be used to pull the balloon distally to tension it, with the bonded proximal end of the balloon holding firm. In one implementation the balloon is stretched by about five millimeters beyond its unbiased (untensioned) length. As the balloon is held stretched (tensioned), an air gun can be used to dry the heptanes from under the balloon distal neck 704. As shown in FIG. 12, the flared end 722 of the second piece of heat shrink tubing 724 referred to briefly above is slid over the balloon distal neck 704 such that the flared end 722 covers the distal conical segment 708 of the balloon 700 to protect it during bonding. The catheter is once again engaged with the clamping fixture and secured using a rubber clamp. The clamp fixture is engaged with the heating components of the bonding machine and the bonding machine activated according to the settings established above to bond the distal end of the balloon to the catheter in part aided by the heat shrink tubing. After bonding, the catheter is removed from the bonding machine and allowed to cool.

Excess heat shrink tubing is them removed and if desired the balloon bonds are ironed by once again sliding a piece of heat shrink tubing over the proximal neck 702 of the balloon, placing the portion of the catheter supporting the proximal neck into the clamping fixture of the bonding machine, and heating the portion of the catheter supporting the proximal neck for, e.g., four seconds. The clamping fixture is then manipulated to release the catheter and the catheter rotated ninety degrees (by, e.g., hand), re-engaged with the clamping fixture and reintroduced into the bonding machine and heated once again. The catheter is them removed from the machine and excess heat shrink tubing skived away. The distal neck of the balloon may be similarly ironed.

While the particular AORTIC OCCLUDER WITH TENSIONED BALLOONS is herein shown and described in detail, it is to be understood that the subject matter which is encompassed by the present invention is limited only by the claims.

What is claimed is:

1. A catheter, comprising:
an elongate member having proximal and distal ends and proximal and distal regions;
at least a first expandable member mounted on the distal region of the elongate member, the first expandable member being inflatable with fluid through at least one lumen in the elongate member to cause the first expandable member to expand from an empty configuration to an expanded configuration, the first expandable member being disposed on the elongate member in first tension such that the first expandable member is preloaded with tensile stress in the empty configuration;
at least a second expandable member mounted on the distal region of the elongate member, the second expandable member being inflatable with fluid through at least one lumen in the elongate member to cause the second expandable member to expand from an empty configuration to an expanded configuration, the second expandable member being disposed on the elongate member in second tension such that the second expandable member is pre-loaded with tensile stress in the empty configuration, the first and second tensions being different from each other.

2. The catheter of claim 1, further comprising:
at least a first heat-shrink tube disposed around a first end segment of the first expandable member and at least a second heat-shrink tube being disposed around a second end segment of the first expandable member to hold the first expandable member in tension on the elongate member;
the second expandable member being mounted on the elongate member proximal the first expandable member; and
at least a third heat-shrink tube disposed around a first end segment of the second expandable member and at least a fourth heat-shrink tube being disposed around a second end segment of the second expandable member to hold the second expandable member in tension on the elongate member.

3. The catheter of claim 2, wherein the first and second expandable members are balloons.

4. The catheter of claim 2, wherein the second expandable member is disposed in less stress on the elongate member than the first expandable member.

5. The catheter of claim 1, further comprising a port formed in the elongate member and communicating with a pressure monitoring lumen in the elongate member for establishing fluid communication between the port and a pressure monitoring device engageable with the pressure monitoring lumen.

6. The catheter of claim 1, wherein the first expandable member comprises a body, a first end segment that is radially smaller than the body, and a conical segment connecting the first end segment to the body.

7. The catheter of claim 2, wherein the first heat shrink tube comprises a first end segment closely surrounding the first end segment of the first expandable member and a conical segment closely surrounding a conical segment of the first expandable member.

8. The catheter of claim 1, wherein the proximal region of the elongate member provides stability to prevent migration during use.

9. The catheter of claim 1, wherein, during use, the distal region allows the elongate member to conform to a portion of a patient's aorta while the first expandable member is positioned in the portion of the aorta and is at least partially expanded to increase cerebral perfusion.

10. The catheter of claim 9, wherein the portion of the aorta is the descending aorta.

11. A medical device for partial aortic occlusion for cerebral perfusion augmentation, comprising:
a catheter body; and
at least a first expandable balloon disposed on the catheter body in tension prior to expansion of the first expandable balloon under the influence of an inflation fluid; and
at least a second expandable balloon disposed on the catheter body in tension prior to expansion of the second expandable balloon under the influence of an inflation fluid, the second expandable balloon being disposed in tension on the catheter body in less stress than the first expandable balloon.

12. The medical device of claim 11, wherein at least a first heat-shrink tube is disposed around a first end segment of the first expandable balloon and at least a second heat-shrink tube is disposed around a second end segment of the first expandable balloon to hold the first expandable balloon in tension on the catheter body.

13. The medical device of claim 11 wherein, during use, the catheter body conforms to a portion of a patient's aorta while the first expandable balloon is positioned in the portion of the aorta and is at least partially expanded to increase cerebral perfusion.

14. The medical device of claim 11, wherein the first expandable balloon comprises a body, a first end segment that is radially smaller than the body, and a conical segment connects the first end segment to the body of the first expandable balloon.

15. The medical device of claim 11, further comprising a port formed in the catheter body and communicating with a pressure monitoring lumen in the catheter body for establishing fluid communication between the port and a pressure monitoring device engageable with the pressure monitoring lumen.

16. The medical device of claim 11, wherein the first expandable balloon comprises a body, a first end segment that is radially smaller than the body, and a conical segment connects the first end segment to the body of the first expandable balloon, at least a first heat-shrink tube being disposed around a first end segment of the first expandable balloon, wherein the first heat shrink tube comprises a first end segment closely surrounding the first end segment of the first expandable balloon and a conical segment closely surrounding the conical segment of the first expandable balloon.

17. The medical device of claim 11, wherein the first expandable balloon is a cylindrical expandable balloon having an outer surface and an enclosed chamber.

18. The medical device of claim 11, further comprising a stiffening element that is insertable into a lumen of the catheter body.

19. The medical device of claim 11, wherein a proximal region of the catheter body provides stability to prevent migration during use.

* * * * *